(12) United States Patent
Chen et al.

(10) Patent No.: US 6,791,012 B1
(45) Date of Patent: Sep. 14, 2004

(54) SALT-TOLERANT TRANSGENIC TURFGRASS

(75) Inventors: Tseh An Chen, Basking Ridge, NJ (US); Shou-Yi Chen, Beijing (CN); Gen-Yun Zhang, New Brunswick, NJ (US); Faith C. Belanger, Piscataway, NJ (US)

(73) Assignee: Rutgers The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/763,330

(22) PCT Filed: Aug. 24, 1999

(86) PCT No.: PCT/US99/20849

§ 371 (c)(1), (2), (4) Date: Mar. 27, 2001

(87) PCT Pub. No.: WO00/11138

PCT Pub. Date: Mar. 2, 2000

Related U.S. Application Data
(60) Provisional application No. 60/097,684, filed on Aug. 24, 1998.

(51) Int. Cl.$^7$ .................... C12N 15/29; C12H 15/82; A01H 5/00; A01H 5/10
(52) U.S. Cl. .................. 800/289; 800/320; 435/419; 435/468
(58) Field of Search ................. 435/419, 468; 800/289, 320, 278, 298

(56) References Cited

U.S. PATENT DOCUMENTS

| | | | |
|---|---|---|---|
| 5,589,617 A | 12/1996 | Nehra et al. | 800/205 |
| 5,780,709 A | 7/1998 | Adams et al. | 800/205 |
| 5,981,842 A | 11/1999 | Wu et al. | 800/298 |
| 6,281,411 B1 * | 8/2001 | Adams et al. | 800/288 |

OTHER PUBLICATIONS

Rathinasabapthi et al. Metabolic engineering of glycine betaine synthesis:plant betaine aldehyde dehydrogenases lacking typic transit peptides are targeted to tobacco chloroplasts where they confer betaine aldehyde. Planta, 1994, vol. 193, pp. 155–162.*
Xiao et al., GenBank Accession No. X69770, Jul. 1996.*
Ahmad, I., et al., "The solute and water relations of *agrostis stolonifera* ecotypes differing in their salt tolerance," *New Phytol.*, 1981, 87, 615–629.
Bilang, R., et al., "The 3'–terminal region of hygromycin–B–resistance gene is important for its activity in *escherichia coli* and *nicotiana tabacum*," *Gene*, 1991, 100, 247–250.
Chetelat, R., et al., "Contrasting response to salt stress of two salinity tolerant creeping bentgrass clones," *J. Plant Nutrition*, 1986, 9(9), 1185–1197.
Christensen, A.H., et al., "Ubiquitin promoter–based vectors for high–level expression of selectable and/or screenable marker genes in monocotyledonous plants," *Transgenic Research*, 1996, 5, 213–218.

Gorham, J., et al., "Solute distribution in *suaeda maritima*," *Planta*, 1983, 157, 344–349.
Guo, Y., et al., "Expression of betaine aldehyde dehydrogenase gene and salinity tolerance in rice transgenic plants," *Science in China*, Oct. 1997, 40(5), 496–501.
Hannon, N., et al., "Evolution of salt tolerance in two coexisting species of grass," *Nature*, Dec. 28, 1968, 220, 1342–1343.
Hanson, A.D., et al., "Betaine accumulation: Metabolic pathways and genetics," in Cellular and Molecular Biology of Plant Stress, J.L. Key, et al. (Eds.), *Alan R. Liss, Inc., New York*, Apr. 15–21, 1984, 71–92.
Hartman, C.L., et al., "Herbicide resistant turfgrass (*Agrostis palustris* huds,) by biolistic transformation," *Bio/Technology*, Sep. 1994, 12, 919–923.
Hitz, W.D., et al., "Determination fo glycine betaine by pyrolysis–gas chromatography in cereals and grasses," *Phytochemistry*, 1980, 19, 2371–2374.
Holmstrom, et al., "Production of the *Escherichia coli* betaine–aldehyde dehydrogenase, an enzyme required for the synthesis of the osmoprotectant glycine betaine, in transgenic plants," *The Plant Journal*, 1994, 6(5), 749–758.
Hui–hunang, Y., et al. "The production and cytogenetical studies of *Oryza sativa–Oryza eichingeri* amphiploid," *Chinese J. of Genetics*, 1997, 24(1), 23–29.
Leigh, R.A., et al., "Assessment of glycinebetaine and proline compartmentation by analysis of isolated beet vacuoles," *Planta*, 1981, 153, 34–41.
Lillus, G., et al., "Enhanced NaCl stress tolerance in transgenic tobacco expressing bacterial choline dehydrogenase," *Bio/Technology*, Feb. 1996, 14, 177–180.
Marcum, K.B., "Salinity tolerance mechanisms of six $C_4$ turfgrasses," *J. Amer. Soc. Hort. Sci.*, 1994, 119(4), 779–784.
McCue, K.F., "Drought and salt tolerance: towards understanding and application," *TECH*, Dec. 1990, 8, 358–362.
McElroy, D., et al., "Contruction of expression vectors based on the rice actin 1 (*ACT1*) 5' region for use in monocot transformation," *Mol. Gen. Genet.*, 1991, 231, 150–160.
Nakamura, T., et al., "Expression of a betaine aldehyde dehydrogenase gene in rice, a glycinebetaine nonaccumulator, and possible localization of its protein in peroxisomes," *The Plant Journal*, 1997, 11(15), 1115–1120.

(List continued on next page.)

Primary Examiner—David T. Fox
Assistant Examiner—Cynthia Collins
(74) Attorney, Agent, or Firm—Woodcock Washburn LLP (57) ABSTRACT

A transgenic turfgrass plant expressing a betaine aldehyde dehydrogenase-encoding transgene is provided. The transgenic plant displays significantly increased tolerance to salinity than does its non-transgenic equivalents. The plant also displays increased tolerance to drought conditions. The salt- and drought-tolerant transgenic turfgrass may be planted in regions of high salinity, such as seaside, or in regions where irrigation water is scarce.

13 Claims, 2 Drawing Sheets

OTHER PUBLICATIONS

Rathinasabapodhi, B., et al., "Choline monoxygenase, an unusual iron–sulfur enzyme catalyzing the first step of glycine betaine synthesis in plants: prosthetic group characterization and cDNA cloning," *PNAS*, 1997, 94, 3454–3458.

Rathinasabapathi, et al., "Cultivated and wild rices do not accumulate glycinebetaine due to deficiencies in two biosynthetic steps," *Crop Science*, May–Jun. 1993, 33, 534–538.

Rhodes, D., "Quaternary ammonium and tertiary sulfonium compounds in highter plants," *Annu. Rev. plant physiol. Plant mol. Biol.*, 1993, 44, 357–384.

Trossat, et al., "Transgenically expressed betaine aldehydrogenase efficiently catalyzes oxidation of dimethylsulfoniopropionaldehyde and w–aminoaldehydes," *Plant Physiology*, 1997, 113, 1457–1461.

Weretilnyk, E.A., et al., "Molecular cloning of a plant betaine–aldehyde dehydrogenase, an enzyme implicated in adaptation to salinity and drought," *PNAS*, Apr. 1990, 87, 2745–2749.

Weretilnyk, E.A., "Betaine aldehyde dehydrogenase from spinach leaves: purification, in vitro translation of the mRNA, and regulation by salinity," *Archives of Biochem. And Biophy.*, May 15, 1989, 271(1), 56–63.

* cited by examiner

BEST AVAILABLE COPY

Fig. 2B

SALT-TOLERANT TRANSGENIC TURFGRASS

This application claims priority to U.S. Ser. No. 60/097,684, filed Aug. 24, 1998, the entirety of which is incorporated by reference herein

FIELD OF THE INVENTION

This invention relates to the field of plant breeding, stress tolerance and plant transformation methods. More specifically, transgenic turfgrass is provided, which is salt and drought tolerant by virtue of expressing a transgene encoding betaine aldehyde dehydrogenase.

BACKGROUND OF THE INVENTION

Various scientific and scholarly articles are referred to in parentheses throughout the specification. These articles are incorporated by reference herein to describe the state of the art to which this invention pertains.

Environmental stress is one of the most important factors limiting turfgrass growth and survival. Drought and soil salinity are two of the foremost environmental problems. As world population increases, the acreage of turfgrasses expands also. Turfgrass is used in almost all recreation and athletic fields. Because of limited cultivable lands, more turfgrass acreage has been developed in arid or semiarid regions where soil and water salinity are always a problem for plant growth. In recent years, more and more turfgrass stands are cultivated near bodies of salt water, for example, seaside golf courses. The use of salts for deicing highways, sidewalks and airport runways is another example of increasing soil salinity. Thus, increasing environmental stress tolerance, especially drought and salt tolerance, has been one of the major objectives in turfgrasses breeding programs.

Under drought or salt stress, glycine betaine is accumulated in cells of some higher plants and animals as an osmoprotectant (Hanson and Grumet, 1985, In *Cellular and Molecular Biology of Plant Stress*, ed. J. L. Key, T. Kosuge, pp.71–92, New York: Alan R. Liss, Inc.). Its possible physiological functions, biosynthetic pathways and synthesis-related genes have been studied (Rhodes, 1993, Annu. Rev. Plant Physiol. Plant Mol. Biol. 44:357–384; McCue and Hanson, 1990, TECH 8:358–62). Recently, glycine betaine synthesis-related genes have been isolated (Wrertilnyk and Hanson, 1990, PNAS 87:2745–2749; Xiao et al., 1995, Chinese Science Bulletin. 40(8):741–745; Rathinasabapodhi et al., 1997, PNAS 94:3454–3458). Efforts have been made to increase the activity of betaine synthesis related enzymes through gene transformation in plants in order to increase the glycine betaine accumulation and further improve their drought and salt-tolerance. Transgenic plants of tobacco, rice and strawberry, engineered to overexpress the gene encoding betaine aldehyde dehydrogenase (BADH), have shown improvement in salt tolerance (Holmstrom et al., 1994, The Plant J. 6(5):749–758; Liu et al., 1997, Acta Genetic Sinica. 24(1):24–28; Guo et al., 1997, Science in China 40:496–501). However, no turfgrass as yet has been engineered to overproduce BADH, and so improved salt tolerance in turfgrass has not been achieved by this mechanism. Inasmuch as each genus of plant, especially monocotyledonous plants (which have proven more recalcitrant to tissue culture, regeneration and transformation than dicotyledonous plants), has its own specific requirements for transformation and/or regeneration, it is of significant agronomic and economic importance to develop an efficient turfgrass transformation system, and further to generate salt tolerant turfgrass species using such a system.

SUMMARY OF THE INVENTION

The invention provides transgenic turfgrasses having increased salt tolerance by virtue of expressing a gene involved in the biosynthesis of glycine betaine, an osmoprotectant.

According to one aspect of the invention, a transgenic cell of a Graminaceous plant is provided, which comprises a transgene encoding an enzyme of the glycine betaine biosynthetic pathway. In a preferred embodiment, the transgene encodes betaine aldehyde dehydrogenase from *Atriplex hortensis*, and in a most preferred embodiment, plasmid pRTT120 comprises the transgene. The transgenic cell is preferably a turfgrass, and most preferably selected from the group consisting of Creeping Bentgrass, Perennial Ryegrass, Kentucky Bluegrass, and Bermudagrass.

A salt-tolerant Graminaceous plant produced from the aforementioned transgenic cell is also provided. Preferably, this salt-tolerant turfgrass is also drought-tolerant. Seeds produced from the salt-tolerant turfgrass are also provided.

According to another aspect of the invention, a salt-tolerant transgenic Graminaceous plant is provided which expresses a transgene encoding an enzyme of the glycine betaine biosynthetic pathway. Preferably, the plant expresses a transgene encoding betaine aldehyde dehydrogenase from *Atriplex hortensis*, and most preferably pRTT120 comprises the transgene.

The salt-tolerant transgenic Graminaceous plant is also preferably drought-tolerant, and preferably is selected from the group consisting of Creeping Bentgrass, Perennial Ryegrass, Kentucky Bluegrass and Bermudagrass. Seeds of the transgenic plant are also provided.

Another aspect of the present invention is a transgenic Graminaceous plant with improved phenotypic characteristics. This transgenic plant has at least one of the following characteristics: higher BAH activity, a higher concentration of glycine betaine and a higher growth rate under salt stress, and a higher level of drought tolerance.

Other features and advantages of the present invention will become apparent from the drawings, detailed description and examples that follow.

BRIEF DESCRIPTION OF THE DRAWINGS

FIG. 2. Comparison of the salt damage effect between transgenic and non-transgenic plants, expressed as the percentage of dead, damaged and healthy leaves after 3 weeks treatment. FIG. 2B), 1.2% NaCl stress. Of the pairs of bars on each graph, the left is control and the right is transgenic. Each bar represents the mean value, and error bars represent standard error.

DETAILED DESCRIPTION OF THE INVENTION

I. Definitions

Various terms relating to the methods and compositions of the present invention are used hereinabove and also throughout the specifications and claims.

As used herein, the term "tolerant" or "tolerance" means the ability of a plant to overcome, completely or to some degree, the detrimental effect of an environmental stress or other limiting factor. In the instant case, the transgenic plants are tolerant to high environmental salt concentrations by virtue of producing an abundance of betaine glycine, which functions in the cell as an osmoprotectant.

In this invention, the term "selectable marker" refers to a gene product that confers a selectable phenotype, such as antibiotic resistance, on a transformed cell or plant. Selectable markers are encoded by expressible DNA sequences, which are sometimes referred to herein as "selectable marker genes."

In this invention, the term "promoter" or "promoter region" refers to the 5' regulatory regions of a gene, including promoters per se, as well as other transcriptional and translational regulatory sequences.

Other definitions are as follows. The term "operably linked" means that the regulatory sequences necessary for expression of the coding sequences are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "transgene" refers to an artificial gene which is used to transform a cell of an organism, such as a bacterium or a plant.

When used herein in describing components of media or other experimental results, the term "about" means within a margin of commonly acceptable error for the determination being made, using standard methods. For tissue culture media in particular, persons skilled in the art would appreciate that the concentrations of various components initially added to culture media may change somewhat during use of the media, e.g., by evaporation of liquid from the medium or by condensation onto the medium. Moreover, it is understood that the precise concentrations of the macronutrients, vitamins and carbon sources are less critical to the efficacy of the media than are the micronutrient, hormone and antibiotic concentrations.

In regards to the present invention, statistical significance of quantified differences is determined using one-way analysis of variance (ANOVA) This statistical test is well known to those in the art, and computer programs that carry out this test are commercially available. The level of probably (P) used is 0.05 in a preferred embodiment, 0.01 in a more preferred embodiment, and 0.001 in a most preferred embodiment.

In regards to the present invention, "equivalent plants" are ones of the same genotype or cultivar, at the same age, and having been grown under the same conditions. In the case where one is a transgenic plant, the equivalent plant may be transformed by a similar DNA construct but without the critical transgene, or may not be transformed but regenerated from tissue culture.

II. Description

In accordance with the present invention, transgenic turfgrasses are provided that have increased salt tolerance. In a preferred embodiment, this invention provides transgenic bentgrass carrying the betaine aldehyde dehydrogenase transgene, which are highly salt tolerant. Herein we use the abbreviation BADH and BADH to indicate the betaine aldehyde dehydrogenase gene and gene product, respectively.

The existence of glycine betaine in Graminaceae (also known as Poaceae) has been reported (Hitz and Hanson, 1980, Phytochemistry 19:2371–2374). Some species show glycine betaine accumulation under salt or drought stress and the amount of accumulation is sufficient to produce effective osmotic protection (Marcum and Murdoch, 1994, J. Amer. Soc. Hort. Sci. 119:779–84). Recently, the genes conferring the two enzymes in the biosynthetic pathway of glycine betaine have been isolated. The BADH gene has been cloned from Mountain Spinach, *Atriplex hortensis*, which grows on the shore of a salt lake in western China. In an exemplary embodiment of the present invention, we have successfully transformed Creeping Bentgrass with a Mountain Spinach BADH transgene, and have shown that the ratio of BADH activity and betaine content increased in the transgenic bentgrass.

Under 1.2% NaCl stress, the glycine betaine concentration in the transgenic plants reached 5,891 $\mu$g/g dry weight, which was 74.5% higher than that in the nontransgenic plants. Glycine betaine is considered to be located entirely in the cytoplasm (Gorham and Jones, 1983, Planta 157:344–349). The relative contribution of glycine betaine to osmotic adjustment can be estimated by assuming that the cytoplasmic volume in mature bentgrass mesophyll cells is about 10% of total cell volume (Leigh et al., 1981, Planta 153:34–41), and that the osmotic coefficient of glycine betaine is 1. Using this method, the contribution of glycine betaine in the transgenic plants is estimated to be 360 mOsmol·kg$^{-1}$ higher than that in the non-transgenic plants (830 mOsmol·kg$^{-1}$ for the transformants and 470 mOsmol·kg$^{-1}$ for the controls). This is likely to be the reason for the improved in salt tolerance of the B4 transformants at both the cellular and whole plant levels. In the studies leading to the present invention, BADH activity was not induced by stress.

Although betaine accumulation itself is nontoxic in plants, its synthesis is energetically expensive and may cause possible side effects, such as susceptibly to attack by certain pathogenic fungi and aphids (Strange et al., 1974, Physiol. Plant Path. 4:277–290; Zuniga and Corcuera, 1987, Phytochemistry 26:367–369). Placing coding sequences of betaine synthesis-related genes under the control of an osmotically responsive promoter is a useful strategy contemplated in this invention.

It has been determined previously that the mechanisms of salt tolerance in the highly salt tolerant grasses involve osmotic adjustment, ion exclusion, ion compartmentation, and in some cases, secretion of excess salt (Marcum and Murdoch, 1994, J. Amer. Soc. Hort. Sci. 119:779–84; Hannon and Bradshaw, 1968, Nature 220:1342–1343; Chetelat and Wu, 1986, J. Plant Nutrition 9(9):1185–97). Ion exclusion and possibly ion compartmentation have been demonstrated in the Creeping Bentgrasses (Ahmad et al., 1981, New Phytol. 87:615–629).

The experiments reported herein also suggested that salt tolerance in bentgrass involved mechanisms other than osmotic adjustment. On 0.5% NaCl callus medium, the growth inhibition of the non-transformed controls is very obvious. On 0.8% NaCl medium, non-transgenic callus cells began to lyse at the third week, and severe lysis and death occurred at the forth week. Under 0.8% NaCl stress, while percentage of damaged leaves was not significantly different between control and B4 plants, the percentage of dead leaves was significantly greater in the control plants and the B4 plants grew significantly faster. Clearly, the tolerance of plants was stronger than that of callus tissues. Glycine betaine concentration was significantly higher in leaves than callus tissue, while BADH activity was lower in leaves than callus tissue. These results indicated the influence of organ development. The existence of multiple mechanisms of salt tolerance is worth notice when aiming to improve salt tolerance in turfgrasses, whether by traditional breeding methods or new biotechniques. Because of the complex nature of salt tolerance in turfgrasses, it was surprising to observe the marked increase in salt tolerance resulting from over-expression of just a single gene in the betaine biosynthetic pathway.

As described in greater detail in Example 1, salt stress tests in vitro demonstrated that the BADH-transformed callus lines generated by the aforementioned methods showed improved salt tolerance on 0.8% NaCl medium as compared to the control callus tissues. During in planta salt stress tests, one transgenic line showed better salt tolerance than did the others. Both leaves and roots of these plants grew stronger than control plants under saline conditions, particularly under 1.2% NaCl stress. Presumably, position effects of the transgene played a role in the differential salt tolerance observed among transgenic plants, thus emphasizing the importance of selecting and evaluating several transformants from a particular transformation procedure.

In a preferred embodiment, the salt-tolerant transgenic cells of the invention grow significantly faster that equivalent untransformed cells on a 0.8% NaCl medium. In another preferred embodiment, a transgenic plant of the invention grows significantly faster than the equivalent untransformed plant under 1.2% NaCl stress. In another preferred embodiment, the transgenic plant of the invention is significantly more tolerant to drought than equivalent plants.

While not limiting the invention to any one mode, it is likely that the increased BADH activity leads to increased glycine betaine concentration. Additionally, it is likely that increased glycine betaine concentration leads to increased salt tolerance. When grown under normal growth conditions, the transgenic plant of the invention has at least 1.5x, 2.0x or 3.0x more BAH activity than equivalent untransformed plants in en preferred, more preferred and most preferred embodiments, respectively. When grown under normal growth conditions, the transgenic plant of the invention has at least 2x, 4x, or 6x more glycine betaine per dry weight in leaf tissue than equivalent untransformed plants in preferred, more preferred and most preferred embodiments. When grown under 1.2% NaCl stress, the transgenic plant of the invention grows 1.2x, 1.5x or 2.0x faster than the equivalent untransformed plant in preferred, more preferred and most preferred embodiments.

Preferred turfgrasses of the invention (i.e. transgenic and salt tolerant) have been produced from Creeping Bentgrass, *Agrostis palustris* Huds., Perennial Ryegrass (genotype R821) (Lolium spp.), Bermudagrass cv. Tifeagle (*Cynodon dactylon*) and Kentucky Bluegrass genotype 94-301 (*Poa pratensis*). However, due to the reasonably close similarity among various turfgrasses (i.e., in physiology, genome organization, etc.), achieving salt tolerance by transformation with a BADH gene will have broad applicability to many different kinds of turfgrass. Accordingly, the salt tolerance of these grasses can also be improved by transformation with the BADH transgene. Other turfgrasses contemplated for use are the invention include, but are not limited to, Velvet Bentgrass, Hard Fescue, Chewings Fescue, Strong Creeping Fescue and Colonial Bentgrass.

In accordance with the present invention, several other species in Gramineae (or Poaceae) have been transformed with the BADH transgene. The transformation of Perennial Ryegrass (genotype R821) (Lolium spp.), Bermudagrass cv Tifeagle (*Cynodon dactylon*) and Kentucky Bluegrass genotype 94-301 (*Poa pratensis*) are described in Examples 2–4, respectively. Additionally, the transformants of Perennial Ryegrass (genotype R821) have shown enhanced drought tolerance (Example 2). It is contemplated that because four species of Gramineae have been transformed with a BADH transgene, it is a matter of routine experimentation to transform other species with a similar transgene with similar results. Other grass species of particular interest include, but are not limited to, *Dichondra micrantha, Pennisetum clandestinum, Stenotaphrum secundatum, Zoysia japonica,* Agrostis spp., Festuca spp., Lolium spp., Avena spp., Triticum spp., Secale spp., Hordeum spp., Oryza spp., Panicum spp., Saccharum spp., Sorghum spp., Zea spp., Cynodon spp., Zizania spp., Andropogon spp., Schizachyrium spp., Bouteloua spp. and Buchlöe spp. In regards to the present invention, the taxonomic system of Cronquist is used (for Gramineae, see Gould, 1968, *Grass Systematics*, McGraw-Hill, New York, 1968).

Though the *Atriplex hortensis* BADH gene (Xiao et al., 1995, Chinese Science Bulletin 40(8):741–745) is exemplified herein, any other BADH gene can also be used in accordance with the present invention. For instance, the spinach BADH gene (Weretilnyk and Hanson, 1990, PNAS 87:2745–2749) may also be used, as may other BADH genes isolated in the future (especially preferred are BADH genes from monocotyledonous species). Moreover, this invention contemplates the use as transgenes of any gene in the glycine betaine biosynthetic pathway (e.g., choline monooxygenase), or any combination of those genes.

Biolistic delivery of transforming DNA is exemplified herein for transformation of turfgrass. However, other transformation techniques can be used. Other plant transformation methods include Agrobacterium-mediated delivery, PEG treatment of protoplasts, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Bioloay* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The transgenic plants of the present invention may be made by the following transformation/regeneration protocol, based on biolistic delivery of transforming DNA according to the method of Hartman et al. (1994, Bio/Technology 12:919–923). Embryogenic callus is initiated from germinating seeds of a selected turfgrass. After surface sterilization, seeds are planted on a callus medium. The callus medium may contain plant growth regulators such as 2,4-D, BAP, DiCamba and zeatin riboside. The selection, concentrations and ratios of these growth regulators is varied to suit a particular species of plant. The selection of type and concentration of growth regulators is a matter of routine experimentation and is well know to those skilled in the art of tissue culture.

After 6–8 weeks culture in the dark at 25° C., compact embryogenic calli are selected and transferred to new culture plates. The calli are subcultured every 2–3 weeks on the same medium. Samples for bombardment are made consisting of embryogenic callus on filter discs in a plate of callus medium containing 0.6 M mannitol. The samples are kept in the mannitol medium for an appropriate time (e.g., 16 hours) prior to bombardment.

DNA-coated gold particles are prepared as described, e.g., by Christou et al. (1991). Samples are co-transformed with a selected expression vector containing a coding sequence of interest operably linked to appropriate 5' and 3' regulatory regions, and a vector that expresses a selectable marker. The bombardment is carried out using a standard biolistic delivery system. The day following bombardment, the calli are transferred to callus medium without mannitol. After an appropriate period of time (e.g., 1 week), the calli are transferred to callus medium supplemented with the selectable marker (e.g., hygromycin).

After several weeks of growth on the selection medium, the resistant calli are transferred to regeneration medium and placed in the light. The regenerated shoots from the calli usually appear within 4–8 weeks. The young plants are then transferred to standard growth medium, and the regenerating shoots appear in the order of 3 weeks thereafter. Such tissue culture methods and media are well known to persons skilled in the art of plant tissue culture. The aforementioned cultures generally are performed at about room temperature, e.g., 22–26° C., under a light regimen of between about 30 and 70 $\mu mol \cdot m^{-2} \cdot sec^{-1}$.

It should be recognized that the amount as well as the tissue specificity of expression of the transgene of interest in transformed plants can vary depending on the position of their insertion into the nuclear genome. Such position effects are well known in the art. For this reason, several nuclear transformants should be regenerated and tested for expression of the transgene.

The transformation/regeneration formulations and protocol of the present invention can be used to introduce the salt tolerance-conferring transgene or selectable marker gene into a selected Graminaceous plant. Useful transgenes may employ many useful promoters and coding sequences. Examples of useful promoters for either the transgene or selectable marker gene include, but are not limited to, the rice actin promoter, the maize ubiquitin promoter, the maize ADH 1 promoter, the rice or maize tubulin promoters (Tub A, B or C) and the alfalfa His 3 promoter. Several selectable marker genes may be used in this transformation procedure. In addition to hygromycin resistance, other selectable markers genes suitable for use in the present invention are known (e.g., bialaphos resistance).

Using the foregoing methods, this invention provides salt-tolerant transgenic Graminaceous plants, and also is intended to encompass cells and tissues of those plants, including, but not limited to, leaves, stems, shoots, roots, flowers and seeds. In a preferred embodiment, seeds of the transgenic plants are provided.

The plants grown from the aforementioned seeds, or seeds from other Graminaceous varieties, or the progeny thereof, all of which are considered within the scope of this invention, are used in crosses and selection methods to transfer the transgene of interest into other Graminaceous genotypes, cultivars, varieties and the like.

Plants grown from the transgenic seeds of the invention can also be analyzed to detect the presence of the inserted transgene and vector sequences using DNA extraction, cleavage by one or more restriction endonucleases, and analysis, e.g., Southern blotting using probes derived from the transgene. In this manner, the transfer of foreign transgenes into progeny of breeding crosses can be monitored. An example of the use of such detection and monitoring methods is described in greater detail in Example 1.

Transgenic turfgrass that carry and express the aforementioned BADH coding sequences are expected to be highly resistant not only to salt stress, but also to drought stress and cold stress, which are both osmotically regulated, at least in part.

The following example is provided to describe the invention in greater detail. It is intended to illustrate, not to limit, the invention.

EXAMPLE 1

Transformation of Creeping Bentgrass with BADH Transgene to Produce Tolerance to Salt Stress Materials and Methods:

Initiation and maintenance of embryogenic callus. Embryogenic callus was initiated from germinating seeds of Creeping Bentgrass, cv. Crenshaw. After surface sterilization, seeds were planted on Murashige and Skoog medium (MS) supplemented with 30 mM Dicamba (3,6-dichloro-o-anisic acid), 20 mM BAP and 100 mg/l myo-inositol, 30 g/l sucrose and 2.0 g/l Gell-gro, pH 5.80–5.85. After 6–8 weeks culture in the dark at 25° C., compact embryogenic calli were selected and transferred to new culture plates. The calli were subcultured every 2–3 weeks on the same medium.

Transformation and regeneration of transformants. Samples for bombardment consisted of 0.5 g embryogenic callus on 5.5 cm filter discs in plate of callus media containing 0.6 M mannitol. Samples were kept on the mannitol medium for 16 hours prior to bombardment (Vain et al., 1993, Plant Cell Reports 12:84–88). DNA-coated gold particles (1.0 micron diameter) were prepared as described by Christou et al. (1991, Bio/Technology 9:957–962). Samples were co-transformed with pRTT120 (the BADH expression vector), and pAcH, (the hygromycin resistance expression vector).

The bombardment was carried out using a Bio-Rad PDS-1000/He Biolistic Delivery System at 1,100 psi and at a distance of 12 cm. Each dish was bombarded twice. The day following bombardment, the calli were transferred to callus medium without mannitol. After 1 week, they were transferred to the callus medium supplemented with 200 mg/L hygromycin. After 6–8 weeks of growth on the selection medium, the resistant calli were transferred to regeneration-medium and placed in the light. The regenerated shoots from the calli usually appeared within 4–8 weeks. The young plants were transferred to MS media, and the regenerated roots appeared after 3 weeks.

Expression vectors. The BADH cDNA used was isolated from mountain spinach (*Atriplex hortensis*) and its registration number was EMBL X69770 (Xiao et al., 1995, Chinese Science Bulletin 40(8):741–745).

Figure 1:
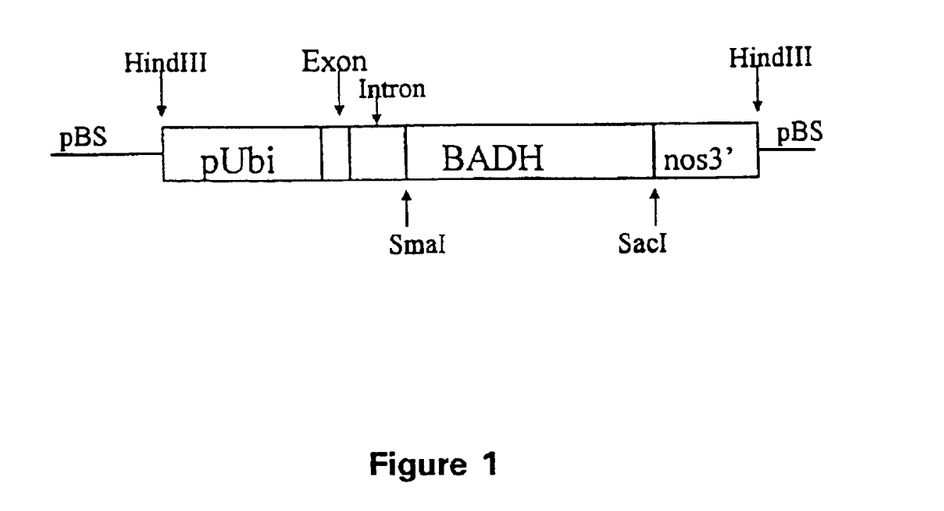
FIG. 1. Schematic representation of the BADH expression vector pRTT120.

The BADH cDNA fragment was inserted into SmaI/SacI site of pAHC25 (Christensen and Quail, 1994, Transgenic Research 5:213–218) replacing the GUS coding sequence. The resulting 4.0 kb Hind III DNA fragment, which contained the 1.6 kb BADH coding sequence flanked by the maize ubiquitin promoter and nos-3' terminal sequence, was then cloned into the Hind III site of pBluescript. The resulting plasmid was designated pRTT120 (FIG. 1). Plasmid pAcHl (provided by Dr. German Spangenberg) contains a truncated hph hygromycin coding sequence (Bilang et al., 1991, Gene 100:247–250) under the control of the rice actin promoter (McElroy et al., 1991, Mol. Gen. Genet. 231:150–160).

BADH activity assay. BADH activity assay was carried out according to Weretilnyk and Hanson (1989, Arch. Biochem. Biophys. 271:55–63). Leaves or callus samples of 1–2 g were homogenized with a pestle in liquid $N_2$ and transferred into the extraction buffer (50 mM Hepes/KOH, pH 8.0, 1 mM EDTA, 5 mM DTT) at 1.0 g sample per 2.5 ml buffer. The homogenate was incubated at 0° C. in an ice bath for 10 min and centrifuged at 13,000×g for 10 min at 4° C. The supernatant was fractionated by 35–70% $(NH_4)_2SO_4$ saturation. The precipitate was collected by centrifugation at 15,000×g for 15 min at 4° C. and the pellet was dissolved in 1.0 ml protein buffer (10 mM Hepes/KOH pH 8.0, 1 mM EDTA, 0.2 mM DTT). The protein concentration was determined by using the Bio-Rad protein assay kit using bovine serum albumin as the standard.

The 1.0 ml reaction system used for BADH activity assay was consisted of 50 mM Hepes/KOH pH 8.0, 5 mM DTT, 1 mM EDTA, 1 mM NAD, 1 mM BADH sample and 0.5 mg protein. The reaction was initiated with the addition of betaine aldehyde chloride and incubated at 37° C. for 20 min. The BADH activity was calculated after determining the absorbance at 340 nm of the reaction products. One unit of enzyme activity was defined as the amount of enzyme needed to convert 1 nmol of NAD per minute under the assay conditions. Calculation of BADH activity was based on an extinction coefficient of 6200 $M^{-1}cm^{-1}$ for NADH.

Betaine content determination. Betaine content was assayed by the periodide method of Pearce et al. (1976, Phytochemistry 15:953–954). Extracted samples were fractionated by thin layer chromatography to check compositions, using the methods of Eneroth and Lindstedt (1965, Anal. Biochem. 10:479–484).

Salinity treatments. The salt tolerance for both transgenic callus tissues and regenerated plants was tested. For callus tests, normal callus medium and the same medium with 0.8% NaCl additive were used. About 0.2 g of both non-transgenic and transgenic calli were transplanted onto a plate containing one of the callus media, and the plate was evenly divided into two parts. After 3 weeks, the calli were carefully removed from the plate and weighed. Three replicates of each treatment were made and the test was repeated three times.

To test the salt tolerance of regenerated plants, 18 normal growing individuals of both non-transgenic and transgenic plants were tested in hydroponic cultivation. Three plastic tubs were filled with 7 liters of Hoagland solution plus ½ strength MS microelements (Hoagland and Arnon, 1938, Univ. Calif. Agr. Expt. Sta. Circ. No.347 (Ch 2)). Six non-transgenic control plants and six BADH+ transgenic plants were transplanted into each tub. The plants were supported with floating styrofoam and the solution in the tub was aerated continuously. Three salt levels (0%, 0.8%, 1.2% NaCl) were used. The plants were allowed to acclimatize to hydroponic conditions for one week before salt was added to the growth solution. The salt was added with an increase of 0.2% NaCl every 3 days until it reached 0.8% and 1.2%, respectively. The plants were allowed to grow in the final salt level for 3 weeks. Nutrient solutions were changed every week. After 3 weeks, the leaves of tested plants were rated. Leaves were divided into dead, damaged or healthy based on whether they were completely dry or wilting, tip burning larger than ⅕ of the leaf length, or nearly no damage, respectively.

Results

Transformation, selection and regeneration of bentgrass. When co-transformation was used, the plasmid ratio between hygromycin resistance transgene and the BADH transgene was 1:1. From 7 transformed dishes, 9 stable hygromycin resistant cell lines were obtained after 8 weeks selection. Shoots appeared for all of the nine cell lines in 6 weeks after the calli were transferred to the regeneration medium. Roots appeared 3 weeks after the shoot were transferred to the Plantcons® half filled with MS medium.

Expression of BADH gene. 0.3–0.5 cm young leaf-tips were used to screen for BADH transgene insertion by PCR (Klimyuk et al., 1993, The Plant J. 3:493–494). Three (B4, B7 and B8) of the nine hygromycin resistant transgenic lines were confirmed to also have the BADH transgene insertion. RT-PCR and BADH activity assay were used to identify the expression of BADH transgene in positive regeneration lines. The ratios of BADH activity in B4, B7 and B8 were 2.9, 2.0 and 8.0 times of the wild type (BADH− control), respectively.

Salinity treatments. All three BADH positive callus lines showed improvement of salt tolerance on 0.8% NaCl medium as compared to the control callus tissues. The appearance and the growth rate of B4 plants was normal while the B7 and B8 plants grew slowly as compared with the non-transgenic plants. The leaf color of B7 was slightly yellowish. Therefore, only B4 callus and regenerated plants were used for further salinity tests.

The fresh weights, ratio of BADH activity and glycine betaine content on normal or 0.8% NaCl medium between transgenic and non-transgenic calli are shown in Table 1. On normal medium, after three weeks culture, the fresh weight of wild type and B4 calli increased 5.12±0.9, and 4.35±0.38 times, respectively, but on 0.8% NaCl medium, the increase was 1.53±0.21, and 3.41±0.42 times, respectively. It appeared that there were some growth inhibition for both wild type and B4 on salt medium. However, the transgenic calli have shown definite improvement of salt tolerance at the cellular level.

On normal growth medium, the glycine betaine content in B4 calli was nearly 8 times higher than that of the control (Table 1.). On 0.8% NaCl medium, although glycine betaine content in the control dramatically increased 9 times, glycine betaine in B4 was still 2.3 times higher than that in the control. Two-dimensional TLC was used to check the composition of glycine betaine extraction from plant materials. The results showed that over 85% of the extraction consisted of glycine betaine plus choline. Since in the assay pure glycine betaine and choline was used as the standard, this result indicated that the periodide method was suitable for the assay.

The ratio of BADH activity in B4 calli was always higher than that of the control. There was no indication that BADH activity in the control or B4 calli was induced, whether they were under short term (2 days) or long term (3 weeks) treatments, although glycine betaine content increased many folds under salt stress. In contrast, a loss of BADH activity was observed, especially for the control under short term treatment.

TABLE 1

Comparison of growth, BADH activity and betaine content between Creeping Bentgrass, cv. Crenshaw transgenic and non-transgenic callus on normal or salt stress (0.8% NaCl) medium.

| | Transgenic callus | Non-transgenic callus |
|---|---|---|
| weight increase on normal medium (times) | 4.33 ± 0.38$^a$ | 5.12 ± 0.90$^b$ |
| weight increase on 0.8% NaCl medium (times) | 3.41 ± 0.42$^c$ | 1.53 ± 0.21$^d$ |
| BADH activity on normal medium U/mg protein) | 764 | 273.9 |

TABLE 1-continued

Comparison of growth, BADH activity and betaine content between Creeping Bentgrass, cv. Crenshaw transgenic and non-transgenic callus on normal or salt stress (0.8% NaCl) medium.

| | Transgenic callus | Non-transgenic callus |
|---|---|---|
| BADH activity on salt medium (U/mg protein) (2 days) | 746.4 | 198.7 |
| BADH activity on salt medium (U/mg protein) (3 days) | 445.7 | 161.1 |
| glycine betaine content on normal medium (µg/g dry weight) | 462.5 | 57.8 |
| glycine betaine content on salt medium (µg/g dry weight) | 1347.8 | 560 |

The growth of plants under different salt concentrations was observed. Under normal conditions, both transgenic and non-transgenic plants grew well and nearly no leaf damage was observed (<1.0%). The root system of non-transgenic grasses was better than that of B4 plants. However, under saline conditions, B4 plants showed better tolerance and both leaves and roots grew stronger than non-transgenic plants, especially under 1.2% NaCl stress.

Figure 2A:
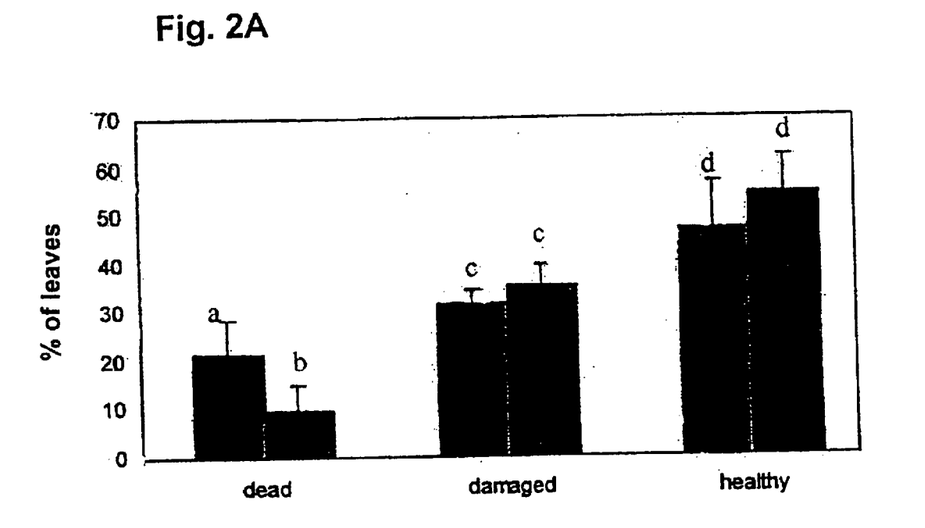
FIG. 2A), 0.8% NaCl stress.
Figure 2B:
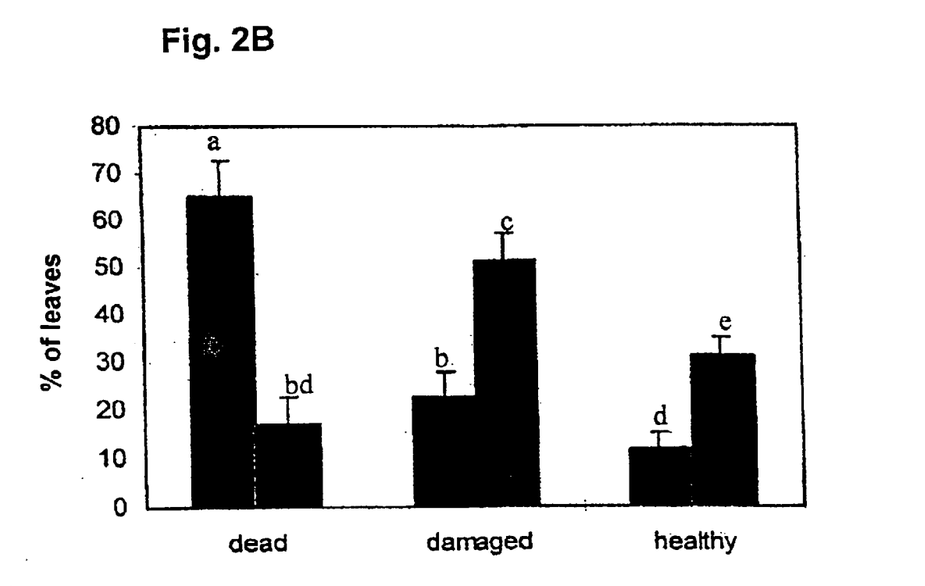

As leaves are the predominant part of turf grass, they were rated as dead, damaged or healthy under different saline conditions. Under 0.8% NaCl stress, there was significant difference on the percentage of dead leaves between B4 and the controls (FIG. 2A). Both B4 and the control grass leaves showed various degrees of damage but the difference was insignificant. B4, however, grew faster than the controls. Under 1.2% NaCl stress, the difference of salt tolerance between B4 and non-transgenic was very significant (FIG. 2B).

TABLE 2

Glycine betaine content, BADH activity of Creeping Bentgrass, CV. Crenshaw transgenic and non-transgenic plants under normal or 1.2% NaCl stress.

| | Transgenic plants | Non-transgenic plants |
|---|---|---|
| glycine betaine content without stress (g/g dry w.) | 4533.4 | 2746.6 |
| glycine betaine content under 1.2% NaCl (g/g dry w.) | 5891.4 | 3375.0 |
| BADH activity without stress (U/mg protein) | 247.0 | 118.1 |
| BADH activity under 1.2% NaCl (2 days) (U/mg protein) | 247.0 | 128.9 |
| BADH activity under 1.2% NaCl (3 days) (U/mg protein) | 112.8 | 161.1 |

Similar to the callus tissues, both the ratio of BADH activity and glycine betaine content of B4 plants were higher than those of controls, whether under normal or 1.2% NaCl stress conditions (Table 2). Under 1.2% NaCl stress, glycine betaine content in B4 plants was 5,891 µg/g dry weight, which was 74.5% higher than that in controls (Table 2).

EXAMPLE 2

Transformation of Perennial Ryegrass with BADH Transgene to Improve Tolerance to Drought Stress Materials and Methods Initiation and maintenance of embryogenic callus. Embryogenic callus was initiated from germinating seeds of Perennial Ryegrass, genotype R821. After surface sterilization, seeds were planted on Murashige and Skoog medium (MS) supplemented with 4.0 mg/L 2,4-D (2,4-dichloro-phenoxyacetic acid), 0.05 mg/L BAP and 100 mg/L myo-inositol, 30 g/L sucrose and 2.0 g/L Gell-gro, pH 5.80–5.85. After 2–3 weeks a culture in the dark at 25° C., compact embryogenic calli were selected and transferred to new culture plates. The calli were subcultured every 2 weeks on the same medium.

Transformation and regeneration of transformants. Plants were transformed and regenerated by the method of Example 1.

Expression vectors. The BADH expression vector of Example 1 was used in the transformation.

BADH activity assay. The BADH activity assay used is described in Example 1.

Drought treatments. For the drought tolerance test, 110 individual plants which came from 110 individual seeds, were randomly selected as control plants to represent the genetic background of genotype R821. Four to six individuals of each transgenic plant line were used as representative of that specific transgenic line. Six of the twenty-seven transgenic lines which showed better drought tolerance in a preliminary test were used in drought test. When plants grew to the 5–10 tiller stage, all the plants were transplanted into two large plastic tubs (23×17 inches), each of which contained 6 inches of fritted clay soaked in Hoagland solution. Holes were drilled at the bottom of the tubs for drainage. The transgenic plants and control plants were randomly arranged and planted in the tubs. Soil and other organic particles adhering to the roots were washed away in tap water before transplantation. Plants were watered every two days. Two weeks after transplantation, plants were mowed to 3 inches height and allowed to grow for another week. All plants were watered thoroughly, and then water was withheld for 18 days.

Arbitrary rating of the wilting leaves based on the degree of water loss and color change of the grasses was used to elucidate the performance of drought tolerance of each individual. In the visual ratings, 1 equaled a total loss of water and color of the leaves and 9 equaled no signs of drought stress. The drought tolerance performance of each plant was scored on the $8^{th}$, $10^{th}$ and $18^{th}$ day after the start of withholding water.

Results

Transformation, selection and regeneration of ryegrass. From 8 dishes of transformed tissues, fifty-two stable hygromycin resistant cell lines were obtained after 8 weeks selection. Six weeks after the calli were transferred to regeneration medium, shoots appeared for forty-eight cell lines. Roots appeared 3 weeks after the shoots were transferred to PlantconS® containing MS medium.

Expression of BADH gene. Young leaf tips (0.3–0.5 cm) were used to screen for BADH transgene insertion by PCR (Klimyuk et al., 1993, The Plant J. 3:493–494). Twenty-seven of the fifty-eight hygromycin resistant transgenic lines were confirmed by Southern blotting to have the BADH transgene insertion. The BADH activity assay was used to identify the expression of BADH transgene in positive regeneration lines. For the six transgenic lines used, the ratios of BADH activity were 1.5 to 3.4 times that of the average of wild type (BADH– control).

Drought treatment. The drought tolerance in control and transgenic plants was determined on the $8^{th}$ day after the withholding water. Statistic analysis showed that among the six transgenic lines used in the test, two transgenic lines had no difference as compared to the controls, while four transgenic lines surpassed the control plants significantly in drought tolerance. The 10$^{th}$ day and 18$^{th}$ day data showed similar results.

EXAMPLE 3

Transformation of Bermudagrass with BADH Transgene

Materials and Methods

Initiation and maintenance of embryogenic callus. Embryogenic callus was initiated from fresh nodes of Bermudagrass, cv. Tif. Eagle. After surface sterilization, nodes were planted on Murashige and Skoog medium (MS) supplemented with 30 mM Dicamba, 20 mM BAP and 100 mg/L myo-inositol, 30 g/L sucrose and 2.0 g/L Gell-gro, pH 5.80–5.85. After 6–8 weeks culture in the dark at 30° C., compact embryogenic calli were selected and transferred to new culture plates. The calli were subcultured every 10 days on the same medium.

Transformation and regeneration of transformants. Samples for bombardment consisted of 0.5 g embryogenic callus on 5.5 cm filter paper discs in a plate with callus media containing 0.6 M mannitol. Samples were kept on the mannitol medium for 16 hours prior to bombardment (Vain et al., 1993, Plant Cell Reports 12:84–88). DNA-coated gold particles (1.0 micron diameter) were prepared as described by Christou et al. (1991, Bio/Technology 9:957–962). Samples were co-transformed with pRTT120 (the BADH expression vector), and pAcH, (the hygromycin resistance expression vector).

The bombardment was carried out using a Bio-Rad PDS-1000/He Biolistic Delivery System at 1,100 psi and at a distance of 9 cm. Each dish was bombarded twice. The day following bombardment, the calli were transferred to callus medium without mannitol. After 1 week, they were transferred to the callus selection medium supplemented with 200 mg/L hygromycin. After 4–6 weeks of growth on the selection medium, the resistant calli were transferred to regeneration medium and placed in the light. The regenerated shoots from the calli usually appeared within 6–8 weeks. The young plants were transferred to MS media, and the regenerated roots appeared after 2 weeks.

Expression vectors. The BADH expression vector was used to transform Bermudagrass, cv. Tif. Eagle plants. The DNA construct is described in Example 1.

Results

Transformation, selection and regeneration of bermudagrass. When co-transformation was used, the plasmid ratio between the hygromycin resistance transgene and the BADH transgene was 1:2. From 6 transformed dishes, twelve stable hygromycin resistant cell lines were obtained after 8 weeks selection. Shoots appeared for all of the nine cell lines in 8 weeks after they were transferred to the regeneration medium. Roots appeared 2 weeks after the shoot were transferred to the PlantconS® half filled with MS medium.

Insertion of BADH gene. Young leaf tips (0.3–0.5 cm) were used to screen for BADH transgene insertion by PCR (Klimyuk et al., 1993, The Plant J. 3:493–494). Five of the twelve hygromycin resistant transgenic lines were confirmed to have the BADH transgene insertion.

EXAMPLE 4

Transformation of Kentucky Bluegrass with BADH Transgene

Materials and Methods

Initiation and maintenance of embryogenic callus. Embryogenic callus was initiated from germinating seeds of Kentucky Bluegrass genotype 94-301. After surface sterilization, seeds were planted on Murashige and Skoog medium (MS) supplemented with 20 mM Dicamba, 0.3 mg/l zeatin riboside and 100 mg/l myo-inositol, 30 g/l sucrose and 2.0 g/l Gell-gro, pH 5.80–5.85. After 6–8 weeks culture in the dark at 25° C., compact embryogenic calli were selected and transferred to new culture plates. The calli were subcultured every 2 weeks on the same medium.

Transformation and regeneration of transformants. Plants were transformed and regenerated by the method of Example 1.

Expression vectors. The BADH expression vector was used to transform Kentucky Bluegrass genotype 94-301 plants. The DNA construct is described in Example 1.

Results

Transformation, selection and regeneration of bentgrass. When co-transformation was used, the plasmid ratio between hygromycin resistance transgene and the BADH transgene was 1:2. From 8 transformed dishes, thirty-six stable hygromycin resistant cell lines were obtained after 8 weeks selection. Shoots appeared for thirty-two cell lines in 6 weeks after the calli were transferred to the regeneration medium. Roots appeared 2 weeks after the shoot were transferred to the PlantconS® containing MS medium.

Insertion of BADH gene. 0.3–0.5 cm young leaf tips were used to screen for BADH transgene insertion by PCR (Klimyuk et al., 1993, The Plant J. 3:493–494). Twenty of the thirty-two hygromycin resistant transgenic lines were confirmed to have the BADH transgene insertion.

The present invention is not limited to the embodiments described and exemplified above, but is capable of variation and modification within the scope of the appended claims.

What is claimed is:

1. A transgenic turfgrass cell comprising a transgene encoding a betaine aldehyde dehydropenase from *Atriplex hortensis*, wherein the cell exhibits increased salt tolerance as compared with an equivalent cell that does not comprise the transgene.

2. The transgenic cell of claim 1, which is selected from the group consisting of Creeping Bentgrass, Perennial Ryegrass, Kentucky Bluegrass and Bermudagrass.

3. The transgenic cell of claim 1, which grows significantly faster on a 0.8% NaCl medium than do equivalent cells that do not comprise the transgene.

4. A transgenic plant produced from the transgenic cell of claim 1, wherein the plant exhibits increased salt tolerance as compared with an equivalent plant that does not comprise the transgene.

5. A transgenic seed produced from the transgenic plant of claim 4, wherein the seed comprises the transgene encoding the betaine aldehyde dehydrogenase.

6. The transgenic plant of claim 4, which grows significantly faster under 1.2% NaCl stress than does an equivalent plant that does not comprise the transgene.

7. The transgenic plant of claim 4, which exhibits increased drought tolerance as compared with an equivalent plant that does not comprise the transgene.

8. A transgenic turfgrass plant comprising a transgene encoding a betaine aldehyde dehydrogenase enzyme from *Atriplex hortensis*, wherein the transgenic turfgrass plant exhibits increased salt tolerance as compared with an equivalent plant that does not comprise the transgene.

9. The transgenic plant of claim 8, which is selected from the group consisting of Creeping Bentgrass, Perennial Ryegrass, Kentucky Bluegrass and Bermudagrass.

10. The transgenic plant of claim 8, which grows significantly faster under 1.2% NaCl stress than does an equivalent plant that does not comprise the transgene.

11. The transgenic plant of claim 8, which also exhibits increased drought tolerance as compared with an equivalent plant that does not comprise the transgene.

12. A seed produced from the transgenic plant of claim 8, which comprises the transgene encoding the betaine aldehyde dehydrogenase.

13. The transgenic plant of claim 11, which is selected from the group consisting of Creeping Bentgrass, Perennial Ryegrass, Kentucky Bluegrass and Bermudagrass.

* * * * *